US00PP30250P2

(12) United States Plant Patent
Van Swieten

(10) Patent No.: US PP30,250 P2
(45) Date of Patent: Feb. 26, 2019

(54) ***PHALAENOPSIS* ORCHID PLANT NAMED 'PHALFLEDJO'**

(50) Latin Name: ***Phalaenopsis* hybrid**
Varietal Denomination: PHALFLEDJO

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/731,737

(22) Filed: Jul. 26, 2017

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHALFLEDJO', particularly characterized by having light purple, spotted and edged flowers with the spots becoming larger toward the center depending on the temperature, 1 to 3 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALFLEDJO'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFLEDJO'.

The new *Phalaenopsis* plant is a product of a planned breeding program conducted by the inventor in Bleiswijk, The Netherlands. The objective of this breeding program was to create a new *Phalaenopsis* plant with numerous attractive and unique light purple, spotted and edged flowers, suitable for potted plant production.

The new *Phalaenopsis* plant 'PHALFLEDJO' is a result of cross-pollination made by the inventor in June 2006 in Bleiswijk, The Netherlands of the proprietary female, or seed parent, *Phalaenopsis* hybrid 'unknown' (unpatented) with the proprietary male, or pollen parent, *Phalaenopsis* hybrid 'unknown' (unpatented). At the time of the crossing the parent plants were known. However, due to a migration of information systems, the original crossing data cannot be determined with certainty. Therefore, the parents are considered to be unknown and no comparison with the female or male parents can be made.

The new *Phalaenopsis* was selected by the inventor as a single plant within the progeny of the stated cross-pollination in a controlled greenhouse in Bleiswijk, The Netherlands in June 2009. Asexual reproduction of the new *Phalaenopsis* plant by meristem tissue culture since 2012 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Sep. 13, 2016. 'PHALFLEDJO' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFLEDJO' as a new and distinct variety of *Phalaenopsis* plant.

1) Light purple, spotted and edged flowers with the spots becoming larger toward the center, depending on the temperature;
2) 1 to 3 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in May 2017. Colors in the photographs may differ from the color values cited in the detailed botanical description, which accurately describe the actual colors of the new variety.

DESCRIPTION OF THE NEW VARIETY

Figure 1:
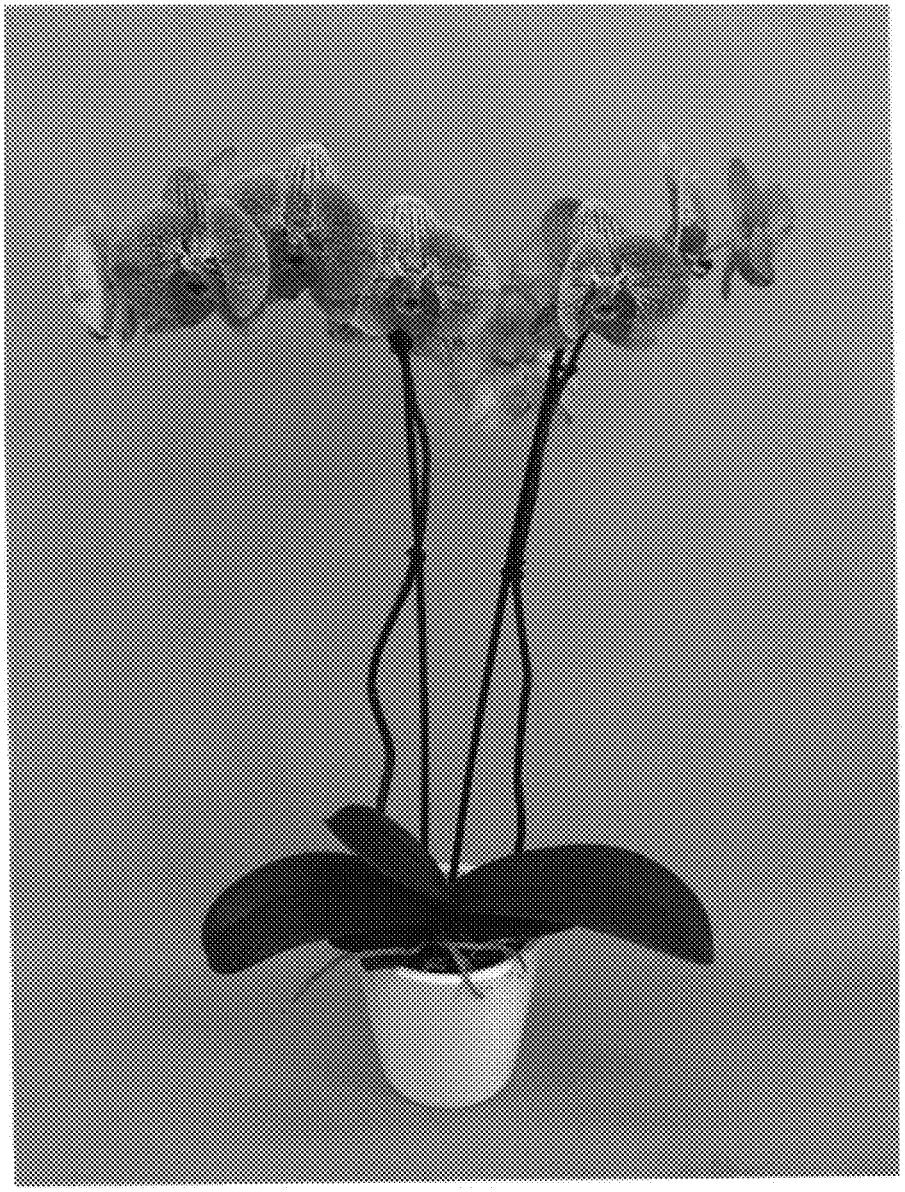
FIG. 1 shows the overall plant habit, including blooms and foliage of 'PHALFLEDJO'.
Figure 2:
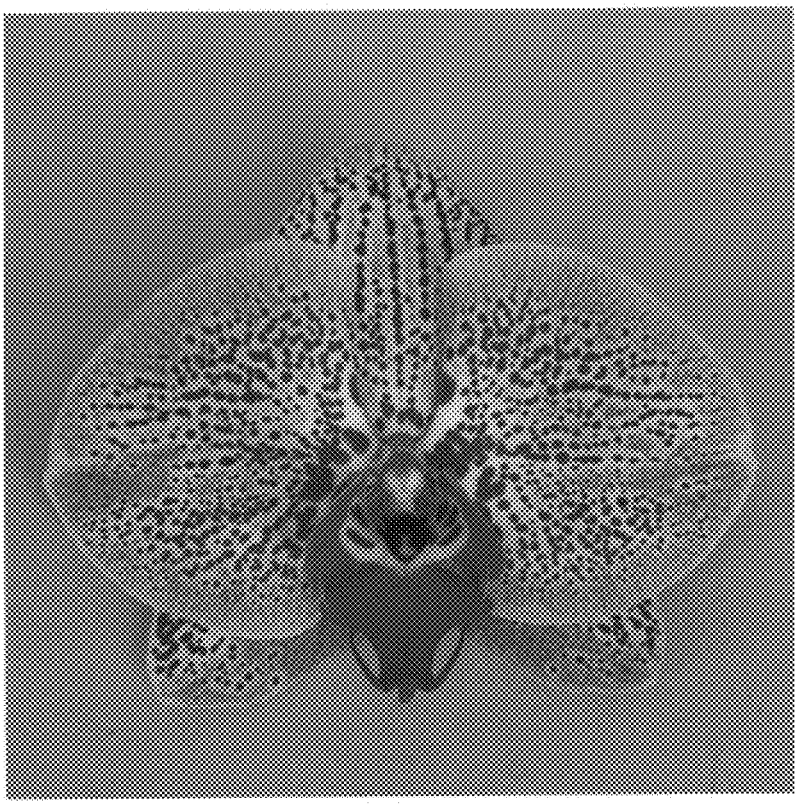
FIG. 2 shows a close-up of a flower of 'PHALFLEDJO'.
Figure 3:
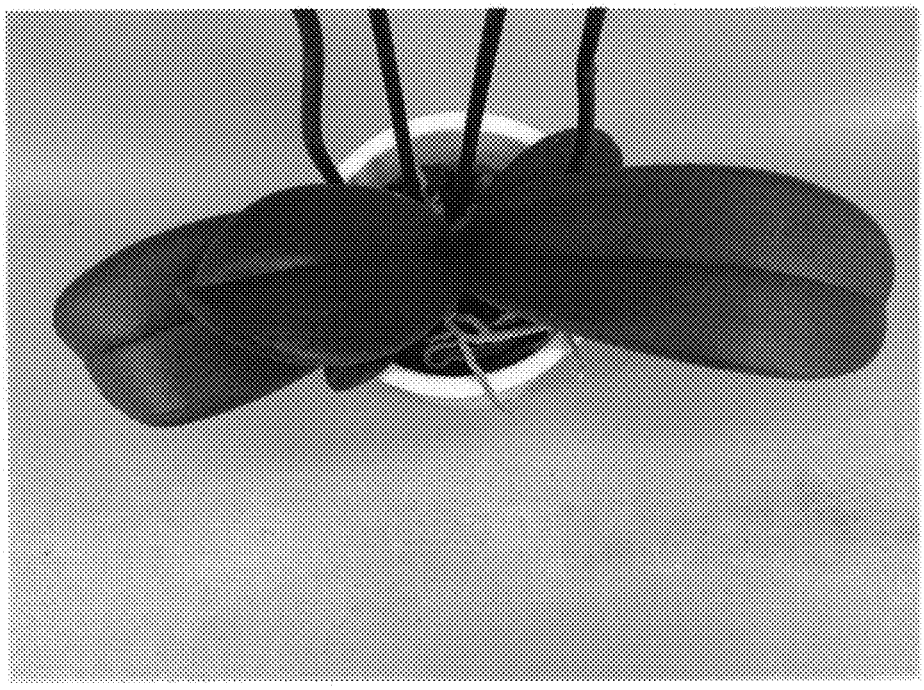
FIG. 3 shows a close-up of the leaves of 'PHALFLEDJO'.

The following detailed description sets forth the distinctive characteristics of 'PHALFLEDJO'. Plants of the new

*Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in May 2017 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFLEDJO'.

Parentage:

*Female parent*.—*Phalaenopsis* cultivar 'unknown' (unpatented).

*Male parent*.—*Phalaenopsis* cultivar 'unknown' (unpatented).

Propagation:

*Type*.—Meristem tissue culture.

Roots:

*Root description*.—Greyed-green colored roots (RHS 190B/C) with branching lateral roots having red-purple colored root tips (RHS 184A).

Plant:

*Commercial crop time to flowering*.—Approximately 48 to 50 weeks from a rooted cutting to finish in a 12 cm pot.

*Growth habit of peduncle*.—Standard, green leaves, raceme to panicle.

*Height* (*from soil level to top of inflorescence*).—Approximately 52.0 cm to 62.0 cm.

*Width* (*measured from leaf tips*).—About 34.0 cm to 36.0 cm.

*Vigor*.—Strong.

Leaves:

*Mature leaves*.—Quantity per plant: 6 to 8 leaves are produced before flowering. Length (fully expanded): 20.0 cm to 22.0 cm. Width: 7.5 cm to 8.5 cm. Shape: Oblong. Base shape: Moderately elongated. Apex: Obtuse unequal. Leaf blade angle with the petiole (measured from the horizontal position): Between 25 degrees and 40 degrees. Leaf margin: Entire. Color: Upper surface: RHS 147A. Lower surface: RHS 147B. Texture (both upper and lower surfaces): Rough. Thickness: 2.4 mm to 2.7 mm. Variegation: Absent. Venation: Pattern: Parallel. Color of the midvein: Upper surface: RHS 147A. Lower surface: RHS 147B.

Peduncle:

*Quantity per plant*.—1 to 3.

*Number of flowers per peduncle*.—8 to 12.

*Length*.—53.0 cm to 63.0 cm.

*Diameter*.—6.2 mm to 6.7 mm.

*Strength*.—Strong.

*Aspect*.—Upright to slightly pendant.

*Texture*.—Smooth.

*Color*.—Brown (RHS N200A) with a touch of very light green (RHS 195A).

*Internode length*.—3.0 cm to 3.5 cm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 170.0 mm to 200.0 mm.

*Number of inflorescences per plant*.—1 to 3.

*Flowering time*.—First flowers can be expected 10 to 11 months after planting in a 12 cm (diameter) pot.

*Flower*.—Height: 90.0 mm to 95.0 mm. Diameter: 98.0 mm to 103.0 mm. Depth of lip: 30.0 mm to 32.0 mm.

*Flower longevity*.—On the plant: 8 to 12 weeks.

*Fragrance*.—Absent.

*Flower bud*.—Average size: Large. Length: 25.0 mm to 27.0 mm. Width: 21.0 mm to 23.0 mm. Shape: Egg shaped. Color: Dark red (RHS 187B) and green (RHS 146B).

*Petals*.—Arrangement: Open/free. Shape: Semi-circular. Apex: Rounded asymmetric. Margin: Entire. Length (from base to tip): 48.0 mm to 50.0 mm. Width: 62.0 mm to 64.0 mm. Position of the broadest part of the petal: Toward the base. Color (when fully opened): Upper surface: Basic color: Light purple (RHS 76B) becoming lighter towards the center (RHS 76D). Over color: Purple edge (RHS N78B) and dark red-purple spots (RHS N79C). Lower surface: Basic color: Light purple (RHS 76B). Over color: White at the base (RHS NN155C) and purple edge (RHS N78C).

*Dorsal sepal*.—Shape: Broad elliptical. Apex: Rounded symmetric. Margin: Entire. Length (from base to tip): 51.0 mm to 53.0 mm. Width: 37.0 mm to 39.0 mm. Color (when fully opened): Upper surface: Basic color: Light purple (RHS 76B). Over color: Purple edge (RHS N78B) and dark red-purple spots (RHS N79C). Lower surface: Basic color: Light purple (RHS 76A). Over color: Purple (RHS N78B).

*Lateral sepals*.—Shape: Ovate. Apex: Obtuse asymmetric. Margin: Entire. Length (from base to tip): 51.0 mm to 54.0 mm. Width: 32.0 mm to 35.0 mm. Color (when fully opened): Upper surface: Basic color: Light purple (RHS 76B). Over color: Purple (RHS N78A) and dark red-purple spots (RHS N79C). Lower surface: Basic color: Light purple (RHS 76B). Over color: Lower half of sepal is purple (RHS N78B).

*Labellum* (*lip*).—Whiskers: Present. Length of whiskers: 23.0 mm to 25.0 mm. Color of whiskers: Purple (RHS N78A) at the base and dark red (RHS 187C) toward the tips. Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Slightly undulated. Length: 21.0 mm to 23.0 mm. Width: 16.0 mm to 18.0 mm. Color: Yellow (RHS 8A) and white at the base (RHS NN155C) with few dark red stripes (RHS 187B); purple (RHS N78A) toward the edge and red-purple on one side (RHS 60A).

*Apical lobe*.—Shape: Triangular. Margin: Entire. Length: 19.0 mm to 21.0 mm. Width: 27.0 mm to 29.0 mm. Color: Small yellow region at the base (RHS 8A), red-purple wings (RHS 60A) and purple (RHS N78B) toward the whiskers.

*Callus*.—Average size: Medium. Height: 0.6 cm to 0.7 cm. Length: 0.6 cm to 0.7 cm. Width: 0.5 cm to 0.6 cm. Color: Dark red (RHS 187A) and yellow (RHS 8A) on the sides.

Reproductive organs:

*Column*.—Length: 8.0 mm to 10.0 mm. Diameter: 5.5 mm to 6.0 mm. Color: Purple (RHS N78B).

*Pollinia*.—Quantity: 2. Diameter: 1.2 mm to 1.4 mm. Color: Orange (RHS 26A).

*Ovary*.—Length: 7.0 mm to 9.0 mm. Diameter: 2.2 mm to 2.4 mm.

*Pedicel*.—Length: 37.0 mm to 39.0 mm. Diameter: 2.5 mm to 2.7 mm. Color: Light purple (RHS N78D) and very light green (RHS 196C).

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL LINES AND MOST SIMILAR VARIETIES

The female and male parent plants of 'PHALFLEDJO' are unknown, so a meaningful comparison cannot be made.

'PHALFLEDJO' is most similar to the commercial *Phalaenopsis* plants named 'PHALFOYX' (U.S. Plant Pat. No. 28,103) and 'PHALCUJOX' (unpatented). 'PHALFLEDJO' differs from the commercial variety 'PHALFOYX' in that 'PHALFLEDJO' has light purple flowers and apical lobes with a small yellow (RHS 8A) region at the base and red-purple wings, whereas 'PHALFOYX' has white flowers and white apical lobes with yellow (RHS 5C/D) at the base and diluting spots. Additionally, 'PHALFLEDJO' has wider apical lobes than 'PHALFOYX'.

'PHALFLEDJO' differs from the commercial variety 'PHALCUJOX' in that 'PHALFLEDJO' has oblong leaves, light purple flowers, and apical lobes with a small yellow region at the base, red-purple wings and purple toward the whiskers, whereas 'PHALCUJOX' has narrow obovate leaves, white flowers, and white and yellow, striped apical lobes. Additionally, 'PHALFLEDJO' has larger flowers than 'PHALCUJOX'.

I claim:

1. A new and distinct variety of *Phalaenopsis* plant named 'PHALFLEDJO', substantially as described and illustrated herein.

* * * * *